US011406482B2

(12) United States Patent
Block

(10) Patent No.: US 11,406,482 B2
(45) Date of Patent: Aug. 9, 2022

(54) URINARY CATHETER OR PLUG AND METHOD FOR MANAGING URINARY INCONTINENCE

(71) Applicant: James C. Block, Raleigh, NC (US)

(72) Inventor: James C. Block, Raleigh, NC (US)

(*) Notice: Subject to any disclaimer, the term of this patent is extended or adjusted under 35 U.S.C. 154(b) by 0 days.

(21) Appl. No.: 17/397,010

(22) Filed: Aug. 9, 2021

(65) Prior Publication Data
US 2022/0047368 A1 Feb. 17, 2022

Related U.S. Application Data

(60) Provisional application No. 63/064,233, filed on Aug. 11, 2020.

(51) Int. Cl.
*A61F 2/00* (2006.01)
*A61M 25/00* (2006.01)
*A61M 25/10* (2013.01)

(52) U.S. Cl.
CPC ............ *A61F 2/0013* (2013.01); *A61F 2/005* (2013.01); *A61F 2/0054* (2013.01);
(Continued)

(58) Field of Classification Search
CPC .... A61F 2/0004; A61F 2/0009; A61F 2/0013; A61F 2/0027; A61F 2210/0071;
(Continued)

(56) References Cited

U.S. PATENT DOCUMENTS 3,610,247 A * 10/1971 Jackson ............ A61M 16/0445
128/207.15
3,841,304 A 10/1974 Jones
(Continued)

FOREIGN PATENT DOCUMENTS

CN 201949183 8/2011
GB 2695728 * 5/2004 ............... A61F 5/44

OTHER PUBLICATIONS

Extended European Search Report, issued in the corresponding European patent application No. 21190444.6, dated Jan. 18, 2022, 7 pages.

*Primary Examiner* — Robert A Lynch
(74) *Attorney, Agent, or Firm* — Hamre, Schumann, Mueller & Larson, P.C.

(57) ABSTRACT

The disclosure provides a device and method for managing urinary incontinence. The device includes a platform, a balloon, and a valve. The platform and balloon can include a silicone material, a thermoplastic material, and an adhesive and/or a cement for sealing the urethra. The thermoplastic and silicone materials can soften at the body temperature so that their shape can be adapted to fit the three-dimensional contour of surfaces of the urethra. The balloon seals the internal orifice of the urethra, and the platform can block the leakage associated with the balloon. The valve permits selective urine voiding. The method includes inserting the device into the urethra and the bladder. The method can also include inflating the balloon. The method can further include pulling the balloon so that the balloon is in sealing contact with the neck of the bladder and moving the platform to a suitable position for sealing the urethra.

25 Claims, 9 Drawing Sheets

(52) U.S. Cl.
CPC . *A61M 25/0017* (2013.01); *A61F 2210/0071* (2013.01); *A61F 2220/005* (2013.01); *A61F 2250/0002* (2013.01); *A61F 2250/008* (2013.01); *A61M 25/0075* (2013.01); *A61M 25/1009* (2013.01); *Y10S 128/25* (2013.01)

(58) Field of Classification Search
CPC ........ A61F 2220/005; A61F 2250/0002; A61F 2250/008; A61M 2025/0018; A61M 25/0017; A61M 25/0075; A61M 25/1009; Y10S 128/25
See application file for complete search history.

(56) References Cited

U.S. PATENT DOCUMENTS

| | | | |
|---|---|---|---|
| 4,432,757 A | | 2/1984 | Davis, Jr. |
| 4,660,560 A | | 4/1987 | Klein |
| 4,710,169 A | | 12/1987 | Christopher |
| 4,932,938 A | | 6/1990 | Goldberg et al. |
| 5,030,199 A | * | 7/1991 | Barwick .............. A61F 2/0018 600/29 |
| 5,090,424 A | | 2/1992 | Simon et al. |
| 5,114,398 A | * | 5/1992 | Trick .................... A61F 2/0013 128/DIG. 25 |
| 5,306,226 A | * | 4/1994 | Salama ................. A61F 2/0009 128/DIG. 25 |
| 5,670,111 A | | 9/1997 | Conway et al. |
| 5,707,357 A | * | 1/1998 | Mikhail ............ A61M 25/0017 604/167.03 |
| 5,724,994 A | | 3/1998 | Simon et al. |
| 5,769,091 A | | 6/1998 | Simon et al. |
| 5,795,288 A | | 8/1998 | Cohen et al. |
| 5,797,877 A | | 8/1998 | Hamilton et al. |
| 5,887,593 A | * | 3/1999 | Levius .................... A61F 5/455 128/885 |
| 6,050,934 A | * | 4/2000 | Mikhail ................ A61F 2/0009 128/DIG. 25 |
| 6,167,886 B1 | | 1/2001 | Engel et al. |
| 6,479,000 B2 | | 11/2002 | Conway et al. |
| 7,037,303 B2 | * | 5/2006 | Beaufore .............. A61F 2/0013 137/849 |
| 7,781,038 B2 | | 8/2010 | Hamilton et al. |
| 9,861,780 B2 | | 1/2018 | Gonzalez |
| 2005/0186370 A1 | * | 8/2005 | Hamilton .............. A61L 29/049 428/35.2 |
| 2005/0256447 A1 | * | 11/2005 | Richardson ....... A61M 5/16813 604/65 |
| 2016/0100927 A1 | * | 4/2016 | Nentwick .......... A61B 17/0401 206/210 |
| 2018/0344249 A1 | * | 12/2018 | McKinney ............. A61B 5/036 |

* cited by examiner

URINARY CATHETER OR PLUG AND METHOD FOR MANAGING URINARY INCONTINENCE

FIELD

The disclosure relates to a device and a method for managing urinary incontinence.

Specifically, the disclosure relates to a urinary catheter or plug for voiding urine controllably while preventing urine leakage and reducing urinary tract infections.

BACKGROUND

The bladder stores urine. During urination, bladder muscles squeeze the bladder, forcing urine out of the bladder through a passage called the urethra. Sphincter muscles around the urethra function as a valve. When the sphincter muscles relax, the urethra is open, and urine can flow out of the bladder. When the sphincter muscles contract, the urethra is closed, and urine cannot flow out of the bladder.

Urinary incontinence is the involuntary leakage of urine. Urinary incontinence can happen when the bladder muscles suddenly contract, and the sphincter muscles are not strong enough to maintain the close of the urethra. Urinary incontinence may also occur if there is a problem with the nerves that control the bladder and urethra.

Urinary incontinence is a common and often embarrassing problem affecting women and men of all ages. Urinary incontinence is more common among women than men. Types of urinary incontinence can include stress incontinence, urge incontinence, overflow incontinence, functional incontinence, and mixed incontinence.

SUMMARY

Embodiments herein provide a device and a method for managing urinary incontinence. In an embodiment, the device comprises one or more materials selected from the group consisting of a silicone material, a thermoplastic material, an adhesive, and a cement. In an embodiment, the silicone and thermoplastic materials are capable of softening at the body temperature of the urethra to be adapted to a shape fitting a contour of an inner surface of the urethra. In an embodiment, the adhesive or cement can hold or bond the device and a urethral mucous membrane or orifice together and sealing gaps therebetween.

In an embodiment, the thermoplastic material is a thermoplastic elastomer that includes at least one selected from the group consisting of styrenic block copolymers, thermoplastic olefin blends (TPO), thermoplastic polyurethanes (TPU), elastomeric alloys (TPV), thermoplastic copolyester (COPE), and polyether block amides (PEBAX), and the like and combinations thereof.

In an embodiment, the adhesive or cement is selected from the group consisting of a silicone adhesive or cement, a hydrocolloid adhesive or cement, and an acrylic adhesive or cement, and the like and combinations or composites thereof.

In an embodiment, the silicone and thermoplastic materials have a hardness in a range of at or about 0 to at or about 80 on the Shore 00 scale of hardness at the body temperature of the urethra. In an embodiment, the silicone and thermoplastic materials have a hardness in a range of at or about 10 to at or about 40 on the Shore 00 scale of hardness at the body temperature of the urethra. In an embodiment, the silicone and thermoplastic materials have a hardness in a range of at or about 40 to at or about 65 on the Shore 00 scale of hardness at the body temperature of the urethra.

In an embodiment, the device further comprises an inner body. In an embodiment, the inner body is made of the silicone material, the thermoplastic material, or a combination thereof. In an embodiment, the inner body is made of a silicone rubber. In an embodiment, the thermoplastic elastomer is provided around the inner body.

In an embodiment, the inner body is an elongated body insertable into a urethra through an external opening of the urethra.

In an embodiment, a platform is disposed around the elongated body and movable axially along the elongated body so that the platform is retained at different positions of the elongated body. The platform is capable of sealing the urethra and blocking microbe entry. In an embodiment, the platform is made of silicone material, thermoplastic material, or a combination thereof. In an embodiment, the platform is made of a silicone rubber.

In an embodiment, the adhesive or cement is provided on a surface of the platform. In an embodiment, the platform includes a first adhering surface containing a first adhesive or cement capable of holding or bonding the device and the urethral mucous membrane or orifice together and sealing gaps therebetween in a releasable and reusable manner. In an embodiment, the platform includes a second adhering surface containing a second adhesive or cement capable of adhering the platform to the elongated body.

In an embodiment, the device further comprises an inflatable balloon capable of sealing the internal orifice of the urethra. In an embodiment, the inflatable balloon includes the silicone material, the thermoplastic material, a combination thereof, which is capable of softening at the body temperature of the bladder. In an embodiment, the thermoplastic material is a thermoplastic elastomer. In an embodiment, the inflatable balloon includes an adhesive capable of holding the balloon and the membrane of the neck of the bladder in a releasable and reusable manner and sealing gaps therebetween.

In an embodiment, the elongated body comprises a proximal portion and a distal portion, and the proximal portion is firmer than the distal portion. In an embodiment, the proximal portion has a hardness in a range of 40 to 100 on the Shore A scale of hardness at body temperature. In an embodiment, the distal portion has a hardness in a range of 0 to 40 on Shore A scale of hardness.

In an embodiment, the device further comprises a valve for control of urinary voiding. In an embodiment, the valve comprises a battery, a coil, a spring, a plunger, and a leaf. In an embodiment, the coil generates an electromagnetic field when electric current flows through the coil, which causes the spring to contract and, in turn, causes the plunger to retract so that the leaf is open to allow urine to flow through the valve. In an embodiment, when the electric current stops flowing through the coil, the coil no longer generates an electromagnetic field, and the spring expands, which in turn causes the plunger to be pushed back so that the leaf is in a closed state to stop urine flowing through the valve.

In an embodiment, the method comprises inserting the device through the external orifice of the urethra, wherein the platform contacts and seal the external urethral orifice. In an embodiment, inserting the device includes inserting the inflatable balloon inside a bladder. In an embodiment, the method further comprises inflating the inflatable balloon. In an embodiment, the method further comprises pulling the balloon so that the balloon is in sealing contact with the neck of the bladder and/or the internal urethral orifice. In an embodiment, the method further comprises adjusting the platform position to seal the external urethral orifice while the balloon seals the internal urethral orifice.

BRIEF DESCRIPTION OF THE DRAWINGS

References are made to the accompanying drawings that form a part of this disclosure, and which illustrate embodiments in which the devices and methods described in this specification can be practiced.

DETAILED DESCRIPTION

The term "a," "an," or "the" cover both the singular and the plural reference, unless the context clearly dictates otherwise. The terms "comprising," "having," "including," and "containing" are open-ended terms, which means "including but not limited to," unless otherwise indicated.

Certain values herein are preceded by the term "about." The term "about" herein provides literal support for the exact value that it precedes, as well as a range that is near to or approximately the value that the term precedes. In an embodiment, the range is from 70% to 130% of the exact value that the term "about" precedes. In an embodiment, the range is from 80% to 120% of the exact value that the term "about" precedes. In an embodiment, the range is from 90% to 110% of the exact value that the term "about" precedes. In an embodiment, the range is from 99% to 101% of the exact value that the term "about" precedes. For example, if the exact value is 100, the range from 70% to 130% of the exact value is 70 to 130.

The disclosure relates to a device and method for managing urinary incontinence. Specifically, the disclosure relates to a urinary catheter or plug for preventing urine leakage and reducing urinary tract infections. The device can be a urinary catheter or plug. The device has the advantage of preventing intraurethral leakage and bladder infections.

Figure 1:
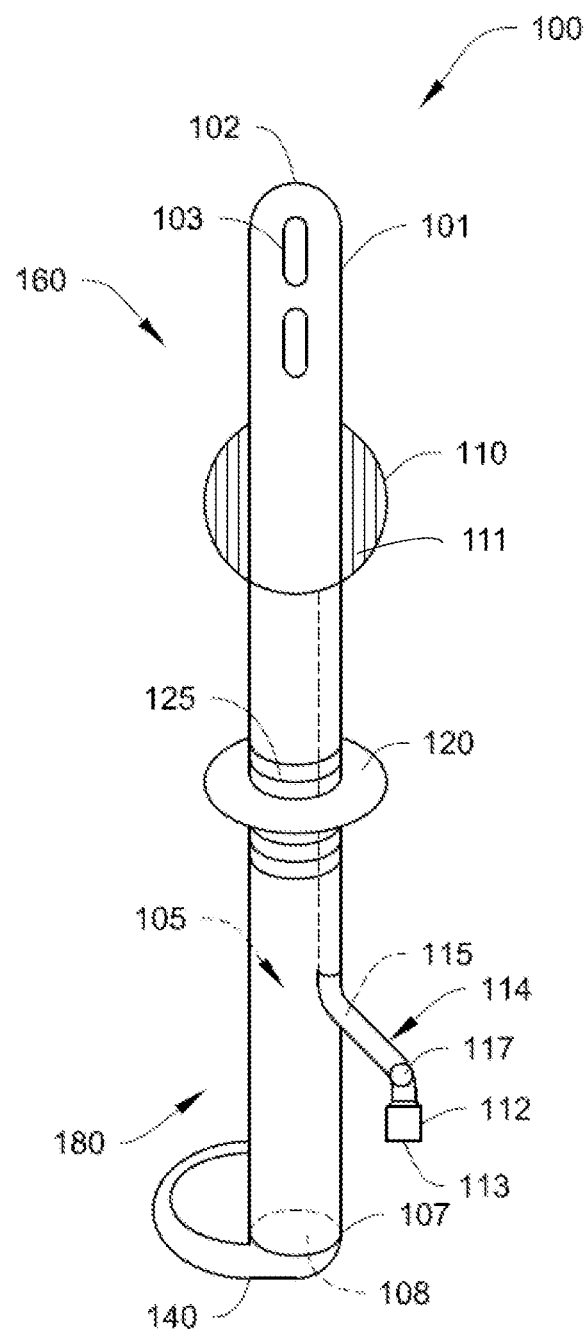
FIG. 1 schematically illustrates a urinary catheter, according to an embodiment.

Referring to FIG. 1, FIG. 1 illustrates a urinary catheter 100 for managing urinary incontinence, according to an embodiment. The urinary catheter 100 can be formed from any suitable non-allergenic, soft material that does not irritate and damage the urethra and bladder tissues but generally firm enough to be inserted into the urethra and bladder. The urinary catheter 100 can address many drawbacks of a traditional Foley type catheter, particularly its relatively high intraurethral leakage rate. The urinary catheter 100 can comprise an elongated body 101 and a platform 120. The platform 120 can act as a plug of the urethra, preventing urine from leaking out of the urethra, blocking bacteria or other microbes from migrating into the bladder, and reducing urinary tract infections (UTI). The platform 120 is provided to seal the urethra so that the urine exits the bladder through the urine passage 105. In an embodiment, when the urinary catheter 100 is in use for managing urinary incontinence, the platform 120 resides at the external urethral orifice. In an embodiment, the platform 120 resides at the distal end of the urethra for sealing the exterior orifice of the urethra. In an embodiment, the platform 120 resides within the urethra for sealing the urethra.

The platform 120 can be made from a silicone material, a thermoplastic material, an adhesive, a cement, a thermo-impression material, or any other suitable non-tissue irritating, non-allergenic material, or a combination thereof. In an embodiment, the suitable non-tissue irritating, non-allergenic material enables the platform 120 to form an impression of the opposing mucosa membrane and/or urethral orifice to obtain a seal or adherence sufficient to prevent urine leakage and bacterial migration into the bladder. In an embodiment, the suitable non-tissue irritating, non-allergenic material is a material that is firm enough to hold the adhesive, cement, and/or thermoplastic material but soft enough not to irritate the involved tissue. The thermos-impression material can include one or more material selected from the group consisting of a polysiloxane thermo-impression material and a polyether thermo-impression material.

In an embodiment, the platform 120 is made of a silicone material or a material containing silicone. In an embodiment, the platform 120 is made of medical-grade silicone. In an embodiment, the platform 120 is made of a silicone rubber. In an embodiment, the platform 120 comprises a silicone rubber. In an embodiment, the platform 120 is coated with a silicone material. In an embodiment, the silicone rubber is a liquid silicone rubber. In an embodiment, the platform 120 can be latex-free.

In an embodiment, the platform 120 is made of a thermoplastic material. In an embodiment, the thermoplastic material is a thermoplastic elastomer. In an embodiment, the platform 120 is constructed from a thermoplastic material. In an embodiment, the platform 120 comprises a thermoplastic material. In an embodiment, the platform 120 includes a thermoplastic material provided on its outer surface. Suitable thermoplastic material includes but is not limited to, for example, styrenic block copolymers (for example, styrene butadiene styrene (SBS), styrene ethylene butylene styrene (SEBS)), thermoplastic olefin blends (TPO), thermoplastic polyurethanes (TPU), elastomeric alloys (TPV), thermoplastic copolyester (COPE), and polyether block amides (PEBAX), and the like and combinations thereof. In an embodiment, the thermoplastic material is capable of holding the platform 120 and the urethral mucous membrane or orifice together without irritating or damaging a tissue thereof.

In an embodiment, the silicone and thermoplastic materials can have a softness (hardness) in a range of at or about 10 to at or about 40 on the Shore 00 scale of hardness at a body temperature. In an embodiment, the silicone and thermoplastic materials can have a softness (hardness) in a range of at or about 40 to at or about 65 on the Shore 00 scale of hardness at a body temperature. In an embodiment, the body temperature is the temperature within the urethra. In an embodiment, the body temperate is the temperature within the bladder. In an embodiment, the body temperature is at or about 36.5° C. to at or about 37.5° C. In an embodiment, the body temperature is at or about 37.06° C.

In an embodiment, the silicone and thermoplastic materials can soften at a body temperature to form the impression of the opposing mucosa and urethral orifice to obtain the seal or adherence sufficient to prevent urine leakage and bacterial migration into the bladder. That is, when the silicone or thermoplastic material is within the urethra, the silicone or thermoplastic material softens and becomes deformable so that the platform 120 can adjust its shape to mate the three-dimensional contour of the inner surface or orifices of the urethra, resulting in an excellent sealing effect. The platform 120 is impermeable to body fluid and urine from the bladder.

In an embodiment, the softness, pliability, and/or elasticity of the platform 120 can be further adjusted by forming cavities or channels within the platform 120. In an embodiment, the softness, pliability, and/or elasticity of the platform 120 can be further adjusted by forming cavities within the silicone and/or thermoplastic material.

The platform 120 can also be formed from a non-allergenic and non-irritating medical material other than or in addition to the silicone and/or the thermoplastic material. In an embodiment, the platform 120 includes a soft, foamed material, which can provide a soft deformable outer surface to fit the inner contour of the urethra.

The platform 120 may or may not contain one or more adhesive or cement on its surface(s). In an embodiment, the platform 120 includes an adhesive or cement. The adhesive or cement can be biocompatible without irritating or damaging the involved tissue. The adhesive or cement can also be releasable and reusable. That is, the adhesive or cement is detachable from an adherence surface and re-adherable to a new surface. In an embodiment, the adhesive is a substance or composition that holds things together. In an embodiment, the adhesive is used so that a patient can pull off the platform 120 and re-adhere the platform 120 by force. In an embodiment, the cement is a chemical compound or composition that bonds two surfaces. In an embodiment, the cement is used so that a patient can use a chemical reaction to attach and/or detach the platform 120, for example, by applying a chemical. The adhesion or bonding can resist the stress and pressure due to the urine in the bladder.

In an embodiment, the platform 120 includes a first adhesive surface containing a first adhesive or cement for adhering the platform 120 to the urethral mucous membrane or orifice and sealing the gaps therebetween.

In an embodiment, the platform 120 includes a second adhesive surface including a second adhesive or cement for adhering the platform 120 to the elongated body 101.

In an embodiment, the first and/or second adhesive surface further includes a thermoplastic material such as, for example, a thermoplastic elastomer to give the adhesion between the platform 120 and the involved tissue more strength and plasticity. In an embodiment, the first and/or second adhesive surface also includes a silicone material to improve the adhesion strength and plasticity. In an embodiment, the first and/or second adhesion surface does not contain a thermoplastic material and/or a silicone material.

The adhesive or cement, including the first and second adhesive or cement, can generally be any suitable adhesive or cement capable of adhering the platform 120 to the urethral mucous membrane and orifice without irritating or damaging involved tissues. The adhesive or cement can be one or more materials selected from a group, including but not being limited to silicone adhesives, hydrocolloid adhesives, acrylic adhesives, elastomeric adhesives, thermoplastic adhesives, acrylic adhesives, emulsion adhesives, and thermoset adhesives, and the like, and/or combinations or composites thereof. The adhesive or cement can also be produced by or obtained from a living organism. In an embodiment, the adhesive or cement is a silicone adhesive or cement. In an embodiment, the adhesive or cement is a hydrocolloid adhesive or cement. In an embodiment, the adhesive or cement is an acrylic adhesive or cement.

The platform 120 can be soft, smooth in texture to avoid damage to the surrounding tissue while inserting or pulling the urinary catheter 100. In an embodiment, the platform 120 can have a softness (hardness) in a range of at or about 0 to at or about 80 on the Shore 00 scale of hardness at a body temperature. In an embodiment, the upper limit of the range of the hardness can be at or about 75, at or about 70, at or about 65, at or about 60, at or about 55, at or about 50, at or about 45, or at or about 40. In an embodiment, the lower limit of the range of the hardness can be at or about 5, at or about 10, at or about 15, at or about 20, at or about 25, at or about 30, at or about 35, at or about 40, at or about 45, at or about 50, at or about 55, or at or about 60.

The elongated body 101 includes a top end 102 and a bottom end 107, viewed from the orientation shown in FIG. 1. The elongated body 101 can be made from a thermoplastic material or silicone material. In an embodiment, the elongated body 101 is made from a thermoplastic elastomer. In an embodiment, the elongated body 101 is made from a silicone rubber.

In an embodiment, the urinary catheter 100 also includes, from the top end 102 to the bottom end 107, a balloon 110, an inflation tube 114, and an inlet 112 for balloon inflation or deflation. In an embodiment, the urinary catheter 100 further includes a plurality of openings 103, a urine passage 105, and/or a urination controller 140.

The urine passage 105 communicates with the openings 103. In an embodiment, the openings can be Murphy eye openings or any suitable opening to allow urine to pass into the elongated body 101. In an embodiment, the elongated body 101 defines an inner lumen that forms the urine passage 105. In an embodiment, the urine passage 105 extends from the top end 102 to the bottom end 107.

When the urinary catheter 100 is in place for managing urinary incontinence, the top end 102, the openings 103, and the balloon 110 are within the bladder. Urine in the bladder can flow into the urine passage 105 through the openings 103 and then exit from the urine passage 105 through the bottom end 107. The top end 102 can be a closed or partially closed end. The top end 102 can have any suitable shape. In an embodiment, the top end 102 has a round shape. The bottom end 107 can include a discharge opening 108 where urine exits the urinary catheter 100.

The balloon 110 is inflatable. When the balloon 110 is inflated, the balloon 110 can seal the internal orifice of the urethra so that urine exits the bladder through the urine passage 105 of the urinary catheter 100, not the urethra. The balloon 110 is in fluid communication with the inlet 112 through the inflation tube 114. The inflation tube 114 defines an inflation lumen 115, through which air or liquid can flow into or out of the balloon 110. In an embodiment, the air or liquid can be injected through the inlet 112 and the inflation lumen 115 to inflate the interior region of the balloon 110. In an embodiment, the inlet 112 is provided with an adapter 113 fitted to a Luer lock or Luer slip of a syringe so that a normal medical syringe can inflate the balloon 110. In an embodiment, the inflation tube 114 is provided with a release device 117 for discharging fluid out of the inflated balloon 110. In an embodiment, the release device 117 enables a rapid release of the fluid from the balloon 110 into the inflation tube 114 and out of the urinary catheter 100. In an embodiment, the release device 117 is a valve. In an embodiment, the release device 117 is a palpitatable valve. As the fluid is released from the balloon 110, the balloon 110 deflates, and the urinary catheter 100 can be safely removed without causing urethral injury. In an embodiment, the fluid is air. In an embodiment, the fluid is water. In an embody, the fluid is an antimicrobial solution. In an embodiment, the fluid is a saline solution.

The device can be removed by deflating the inflated balloon 110 located in the bladder and then gently pulling on the urinary catheter 100, which will release the platform 120.

The balloon 110 can be made from any suitable material. In an embodiment, the balloon 110 is made from a thermoplastic material. In an embodiment, the balloon 110 is made from an elastomer. In an embodiment, the balloon 110 includes a thermoplastic elastomer on its exterior surface. In an embodiment, the balloon 110 is coated with a silicone rubber.

In an embodiment, the platform 120 holds the balloon 110 in a sealing contact with the neck of the bladder. In an embodiment, the balloon 110 includes an adhesion surface provided on a surface 111 where the balloon 110 contacts the neck and/or the internal orifice of the urethra when the balloon 110 is in place for managing urinary incontinence. In an embodiment, the adhesion surface adheres the balloon 110 to the neck and sealing gaps therebetween in a releasable and reusable manner. In an embodiment, the adhesion surface includes an adhesive discussed above.

The distance between the platform 120 and the balloon 110 can be configurable to fit different patients. In an embodiment, a retainer 125 is provided between the platform 120 and the elongated body 101 for adjusting the position of the platform 120. The platform 120 can be movable axially along the retainer 125. In an embodiment, the retainer 125 includes ridges, and the platform 120 can slide axially along the ridges. In an embodiment, the retainer 125 may be threaded, and the platform 120 can move up or down along the thread by rotation. The retainer 125 can retain the platform 120 at different positions of the elongated body 101 so that the urinary catheter 100 can fit different lengths of the urethra.

In an embodiment, the retainer 125 is molded onto the elongated body 101. The retainer 125 can be firm so that it can retain the platform 120. In an embodiment, the retainer 125 is fixed on the elongated body 101 by an adhesive or cement or the like. In an embodiment, the retainer 125 and the elongated body are unitary one piece and constructed from the same material.

The platform 120 can also be preconfigured to have various distances from the balloon 110 to fit various lengths of patients' urethra. In an embodiment, the urinary catheter 100 can be manufactured with different distances between the platform 120 and the balloon 110 to fit various patients' needs. In an embodiment, the urinary catheter 100 does not include the retainer 125, in an embodiment, the platform 120 is directly molded on the elongated body 101. In an embodiment, the platform 120 is directly fixed on the elongated body 101 with an adhesive or cement or the like.

The urinary catheter 100 can be inserted into the urethra and the bladder. After the balloon 110 is inflated through the inlet 112, the urinary catheter 100 is gently pulled so that the balloon 110 can be in firm contact with the neck of the bladder to seal the internal orifice of the urethra. The platform 120 is also advanced along with the urinary catheter 100 to reach a suitable position on the urethral orifice. In an embodiment, the platform 120 is advanced until its adhesion surface contacts the external orifice of the urethra. The platform 120 then softens at body temperature, forming a waterproof seal with the external urethral orifice.

Compared to the traditional Foley type catheter, the platform 120 can prevent urine leakage and reduce bacterial infections due to using an inflatable balloon alone for sealing, as the inflatable balloon of the traditional Foley type catheter has drawbacks in allowing intraurethral leakage. Combining the platform 120 with the balloon 110 can ensure urine exits the bladder only through the urine passage 105 of the urinary catheter 100, not the urethra. The platform 120 and the balloon 110 provide the urinary catheter 100 with advantages over the traditional Foley type catheter, as it can minimize or prevent the urine leakage associated with the traditional Foley type catheter. Although the traditional Foley type catheter may include a structure called collar, the collar is typically disposed outside of the urethra and not in contact with the distal end of the urethra. Thus, the collar is primary for stabilizing the inflatable balloon, not for sealing, even though it may provide an obstacle to leakage at the distal end of the urethra.

The elongated body 101 can be divided into two portions: a proximal portion 160 and a distal portion 180. The proximal portion 160 can be generally disposed within the urethra and bladder. In an embodiment, the distal portion 180 is absent. In an embodiment, the proximal portion 160 is firm and polished. The firmness of the proximal portion 160 enables the insertion of the urinary catheter 100 into the urethra and bladder. In an embodiment, the proximal portion 160 can have a hardness in a range of at or about 40 to at or about 100 on the Shore A scale of hardness at the body temperature. In an embodiment, the proximal portion 160 can also be slightly elastic to provide a comfortable wearing experience. The distal portion 180 can be disposed outside the urethra and bladder. The distal portion 180 can be short in length so that it is hidden and does not interfere with the mobility of a user. In an embodiment, the distal portion 180 is soft and pliable. The softness and pliability of the distal portion 180 enables the urinary catheter 100 to be worn without interfering with the normal activities of the user and without being evident. In an embodiment, the distal portion 180 can have a hardness in a range of at or about 0 to at or about 40 on Shore A scale of hardness at the body temperature.

In an embodiment, the proximal portion 160 and the distal portion 180 are a unitary one-piece construction. In an embodiment, the proximal portion 160 and the distal portion 180 are made from different materials and molded together.

It is appreciated that the distal portion 180 can have the same firmness as that of the proximal portion 160. In an embodiment, the proximal portion 160 and the distal portion 180 have a hardness in a range of at or about 50 to at or about 100 on the Shore A hardness scale at the body temperature. In an embodiment, the proximal portion 160 and the distal portion 180 are unitary one-piece constructed from the same material.

The urination controller 140 can open or close the urine passage 105, permitting selective voiding. When the urine passage 105 is open, urine can be discharged from the bladder. When the urine passage 105 is closed, urine is retained in the bladder.

The urination controller 140 can be or include a plug or valve. When a patient wants to or feels the need to void, he/she can displace the plug or open the valve. After the patient has voided, he/she can replace the plug or close the valve. In an embodiment, the urination controller 140 is a plug that can closely fit and seal the discharge opening 108 of the elongated body 101. In an embodiment, the plug can be plugged into the discharge opening 108 and retained to close the urine passage 105.

In an embodiment, the urination controller 140 can be or include a discharge valve. In an embodiment, the valve is a mechanical valve, including but not being limited to, for example, ball-and-seat valve, duckbill valve, inflatable check valve, dome-type valve, or the like, or any suitable valve. The valve can be operated manually or electronically by the user or patient. In an embodiment, the valve can be a palpitatable discharge valve as a portion of the valve can be squeezed or pressed to open the valve. The palpitatable discharge valve can be orientation-dependent (uniaxial) or orientation independent (multi-axial), based upon whether pressure needs to be applied to a pair of selected points or surfaces in order to open the valve sufficiently for normal discharge operation, or whether the valve will open when pressure is exerted radially from any two opposing directions. In an embodiment, the discharge valve is a uniaxial duckbill valve, which can be rotated between the user's fingers until pressure is directed on the proper sites to maximize fluid flow. In an embodiment, the discharge valve is a palpitatable multi axial dome-type discharge valve.

In an embodiment, the urination controller 140 and the elongated body 101 are separate pieces assembled together. In an embodiment, the urination controller 140 is attached to the elongated body 101 by an adhesive or cement. In an embodiment, the urination controller 140 and the elongated body 101 are not separate pieces. In an embodiment, the urination controller 140 is molded onto the elongated body 101. In an embodiment, the urination controller 140 includes or is a plug, and the plug and the elongated body 101 is a unitary one-piece construction.

In an embodiment, the exteriors of the distal portion 160, the urination controller 140, the inlet 112 comprises a silicone rubber, which can provide an excellent wearing experience. In an embodiment, the silicone rubber is medical latex-free silicone rubber.

It is appreciated that some features discussed above can be optional. In an embodiment, the urinary catheter 100 does not include the inflatable balloon 110. In an embodiment, the urinary catheter 100 does not include the openings 103. In an embodiment, the urinary catheter 100 does not include the openings 103, the inflatable balloon 110, the inlet 112, and the inflation tube 114.

Figure 2:
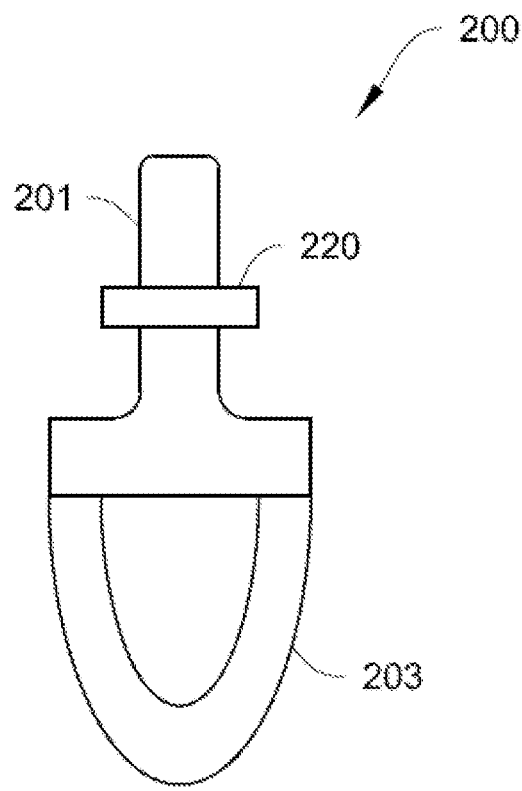
FIG. 2 schematically illustrates a urethral plug, according to an embodiment.

Referring to FIG. 2, FIG. 2 illustrates a urethral plug 200, according to an embodiment. The urethral plug 200 can be inserted into or onto the urethra to block urine from flowing through the urethra. In an embodiment, the urethral plug 200 can include an elongated body 201 and a platform 220.

The elongated body 201 is soft but firm enough to enable the urethra plug 200 to be inserted into the urethra. The material and softness of the elongated body 201 are similar to those discussed above for the proximal portion 160 of the elongated body 101. The features discussed above for the proximal portion 160 of the elongated body 101 is incorporated herewith.

The platform 220 seals the urethra and can be functionally similar to the platform 120 in FIG. 1. The features discussed above for the platform 120 are applicable to the platform 220 and incorporate herewith, unless indicated otherwise. In an embodiment, the platform 220 contacts and seals the external orifice of the urethra. The platform 220 can have material, softness, and structures such as adhesive surface similar to those discussed above for the platform 210.

In an embodiment, a retainer similar to the retainer 125 can also be provided on the elongated body 201 so that the platform 220 can move or slide axially so that the platform 220 can be inserted into different positions of the urethra.

In an embodiment, the elongated body 201 further includes an attachment 203. The attachment 203 can be used to unplug the urethral plug 200 when a patient wants to void or feel the need to void. In an embodiment, the attachment 203 can also facilitate placing the urethral plug 200 into the urethra after the patient voids. In an embodiment, the attachment 203 is a ring. In an embodiment, the attachment is a handle. The attachment 203 is soft and pliable so that it can be worn comfortably without being evident and interfering with the normal activity of the patient. In an embodiment, the material and softness of the attachment 203 are similar to those discussed above for the distal portion 180 of the elongated body 101. In an embodiment, the attachment 203 is made from silicone rubber or liquid silicone rubber.

Figure 3:
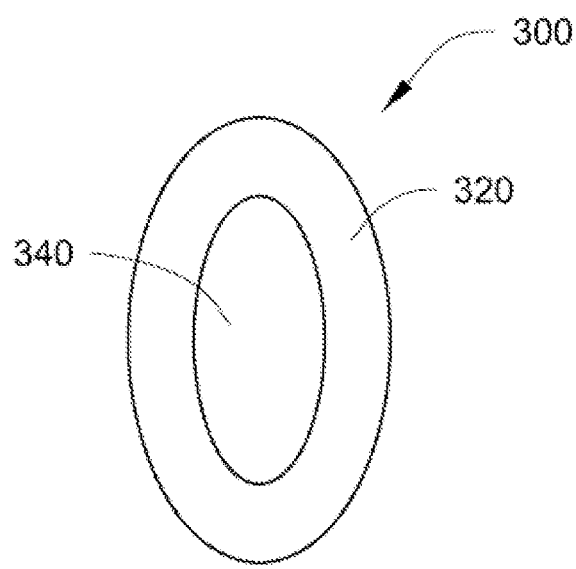
FIG. 3 schematically illustrates a top view of a urethral plug, according to another embodiment.

Referring to FIG. 3, FIG. 3 illustrates a top view of urethral plug 300, according to an embodiment. The urethral plug 300 can be inserted into or onto the external orifice of the urethra, blocking the urethra. The urethral plug 300 comprises a body 320. The body 320 is functionally similar to the platform 120 or 220 discussed above. The body 320 can be made from similar materials discussed above for the platform 120. Thus, the above discussion of the platform 120 or 220 is incorporated herewith. In an embodiment, the urethral plug 300 is composed of the body 320. In an embodiment, the urethra plug 300 further includes an inner body 340. In an embodiment, the body 320 is disposed around the inner body 340. In an embodiment, the inner body 340 is an inner core of the urethral plug 300, and the body 320 constitutes an outermost layer of the urethra plug 300. The inner body 340 can be firm to enable insertion of the urethral plug 300 into the urethra. The inner body 340 can be formed from any suitable materials. In an embodiment, the inner body 340 is formed from a thermoplastic polymer, a silicone material, or a combination thereof. In an embodiment, the thermoplastic polymer is a thermoplastic elastomer. In an embodiment, the silicone material is silicone rubber.

When a user inserts the urethral plug 300 onto or into the urethra, the body 320 contacts the urethral external orifice and/or the mucous membrane and seals gaps therebetween. Like the urethral plug 200, the urethral plug 300 can include an adhesive surface containing an adhesive or cement for holding the body 320 and the urethral external orifice and/or mucous membrane together and sealing gaps therebetween. In an embodiment, the body 320 is soft and can form an impression of the opposing urethral orifice and/or mucous membrane to achieve an excellent seal.

Like the urethral plug 200, the urethral plug 300 is removable whenever the patient wants to void. The adhesion of the adhesive or cement can be releasable and/or reusable. In an embodiment, the adhesive or cement can have a tailorable adhesion time. In an embodiment, the adhesion time is variable depending on the user's hydration and fluid intake.

Figure 4:
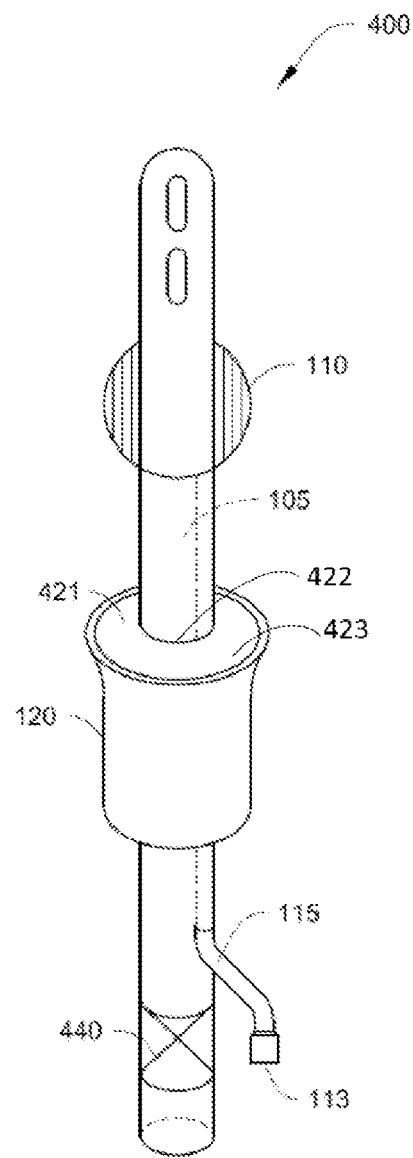
FIG. 4 schematically illustrates a urinary catheter, according to another embodiment.

Referring to FIG. 4, FIG. 4 schematically illustrates a urinary catheter 400, according to another embodiment. The urinary catheter 400 can be structurally similar to the urinary catheter 100. Like the urinary catheter 100, the urinary catheter 400 also includes structural elements such as, for example, the urine passage 105, balloon 110, inflation tube 114, inflation lumen 115, platform 120, urination controller 140, etc. For simplicity of this specification, similar or identical features to those discussed above are not described in further detail.

Compared to the urinary catheter 100, the urinary catheter 400 may not include a retainer disposed between the platform 120 and the elongation body 101. In an embodiment, the platform 120 directly contacts the elongation body 101. In an embodiment, the platform 120 is movable along the elongation body 101. In an embodiment, a user can apply, spray, or paint an adhesive or cement onto the platform 120 or the elongation body 101 and then adjust the platform to a suitable position. When the adhesive or cement takes effect, the platform 120 is adhered to the elongation body 101. In an embodiment, the user applies, sprays, or paints an adhesive or cement onto the platform 120 to adhere the platform 120 to the elongated body 101 after adjusting the platform 120 to a suitable position. In an embodiment, the adhesive and/or cement is pre-coated onto a suitable surface of the platform 120 and protected by a release cover 422, for example a liner, when the urinary catheter 100 is manufactured. The user can peel off the cover 422 to expose the adhesive or cement to adhere the platform 120 to the elongation body 101 before or after adjusting the position of platform 120. As discussed above, the adhesive or cement can be any suitable non-allergenic, non-irritating, biocompatible medical adhesive or cement that can provide sufficient adherence to resist the urine pressure and body movement. In an embodiment, the adhesive or cement is a silicone adhesive or cement. In an embodiment, the adhesive or cement is a non-silicone adhesive or cement. In an embodiment, the adhesive or cement can be selected from the group consisting of a silicone adhesive or cement, a hydrocolloid adhesive or cement, an acrylic adhesive or cement, and a combination or composite thereof.

In an embodiment, the platform 120 is directly and removably glued to the elongation body 101 by, for example, a releasable and reusable adhesive. The releasable and reusable adhesive allows the platform 120 to be moved to a new position at the elongation body 101 by pushing or pulling the platform 120 and then adhered to the new position. In an embodiment, the adhesive is pre-coated onto a surface of the platform 120 when the urinary catheter 400 is manufactured. In an embodiment, the adhesive can be applied onto the surface of the platform when urinary catheter 400 is in use. The releasable and reusable adhesive allows different users to freely adjust and retain the platform 120 to suitable positions at the elongation body 101, providing a comfortable wearing experience.

When the adhesive or cement contacts the elongation body 101, the adhesive or cement can provide sufficient adhesion force to retain the platform 120 and resist the body movement. In an embodiment, the adhesive or cement is coated onto a platform 120's surface that contacts or faces an outer surface of the elongation body 101. In an embodiment, the platform 120's surface directly contacts the elongation body 101.

The platform 120 can further include an adhesive surface 421. The adhesive surface 421 can be an exterior surface that is not directly contacted with the elongation body 101. The adhesive surface 421 not only can adhere the platform 420 to the urethral mucous membrane or orifice but also seal the gaps therebetween.

The adhesive surface 421 contains an adhesive or cement generally discussed above concerning the urinary catheter 100. The adhesive or cement may be the same as or different from the above-discussed adhesive or cement for adhering the platform 120 to the elongation body 101. In an embodiment, the adhesive or cement on the adhesive surface 421 is different from the one for adhering the platform 120 to the elongation body 101. In an embodiment, the adhesive or cement on the adhesive surface 421 is identical or substantially similar to the one adhering the platform 120 to the elongation body 101.

In an embodiment, the adhesive or cement is coated onto the adhesive surface 421 when the urinary catheter 400 is manufactured. In an embodiment, the adhesive surface 421 is covered by a cover 423 such as, for example, a release liner. A user can take or peel off the cover 423 to expose the adhesive surface 421 before or when the urinary catheter 400 is in use. In an embodiment, the adhesive or cement is applied onto the adhesive surface 421 when the urinary catheter 400 is in use.

In an embodiment, the adhesive or cement on the adhesive surface 421 can have a tailorable adhesion time. In an embodiment, the adhesion time is variable depending on the patient's hydration and fluid intake. In an embodiment, the adherence via the adhesive or cement can last several hours. In an embodiment, the adherence can last up to one day. In an embodiment, the adherence can last up to two days or more. It will be appreciated that the adherence can last long enough to meet the user or patient's needs.

Figure 5A:
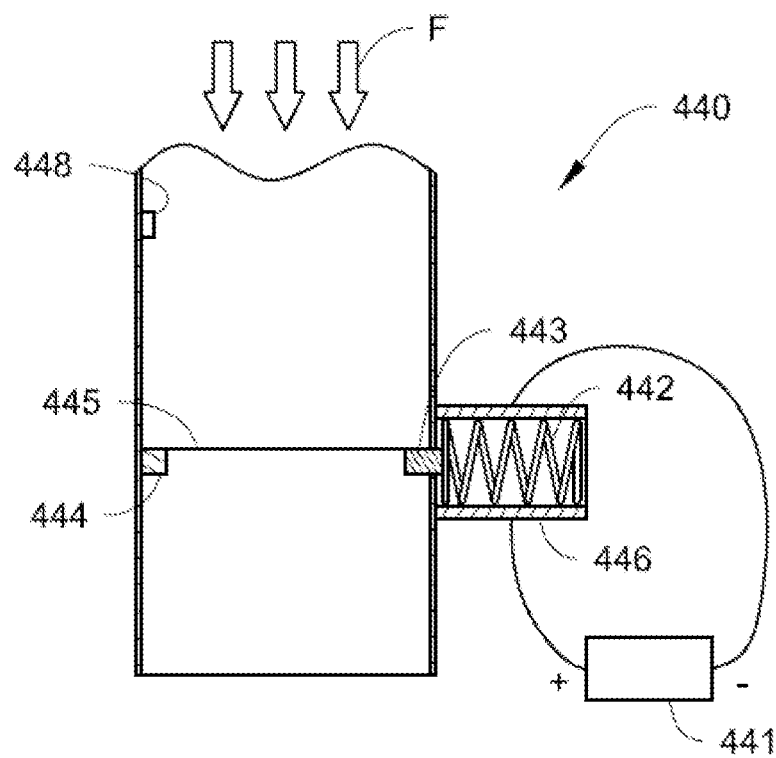
FIG. 5A schematically illustrates a valve in a closed state from a side view, according to an embodiment.

The urinary catheter 400 includes a valve 440. The valve 400 can be disposed within the urinary catheter 400 in whole or portion. The valve 400 can be any type or design suitable and adaptable to use in the urinary catheter 400. The valve 400 can be opened and closed manually, electronically, remotely, or by any suitable means. Referring to FIG. 5A, FIG. 5A schematically illustrates the valve 440 in a closing state, according to an embodiment. The valve 440 can include a spring 442, a plunger 443, a support 444, and a leaf 445. The valve 440 is normally closed. That is, the leaf 445 is normally in a closed position where the leaf 445 is in sealing contact with the support 444 to block the urine flow F from the bladder. A portion of the plunger 443 can extend under the leaf 445 to provide additional support to maintain the leaf 445 at the closed position while the urine pressure within the urinary catheter 400 is increasing. In an embodiment, the leaf 445 is retained to the valve 440 through a hinge 447, along which the leaf can be rotated to the closed position from an open position.

Figure 5B:
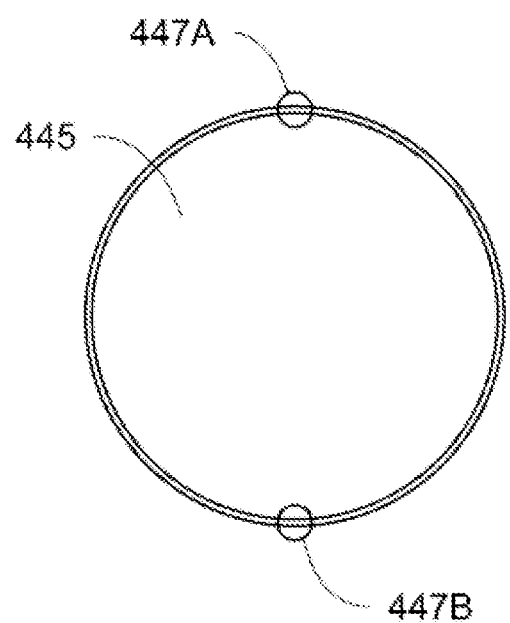
FIG. 5B schematically illustrates a valve in a closed state from a top view along the urine flow F, according to an embodiment.

Referring to FIG. 5B, FIG. 5B schematically illustrates the valve 440 in a closed state from a top view along the urine flow F, according to an embodiment. The leaf 445 is in the closed position, blocking the urine flow F. The hinge 447 can include hinge 447A and hinge 447B acting as rotation pivots for turning the leaf 445 to the closed or open position.

Figure 5C:
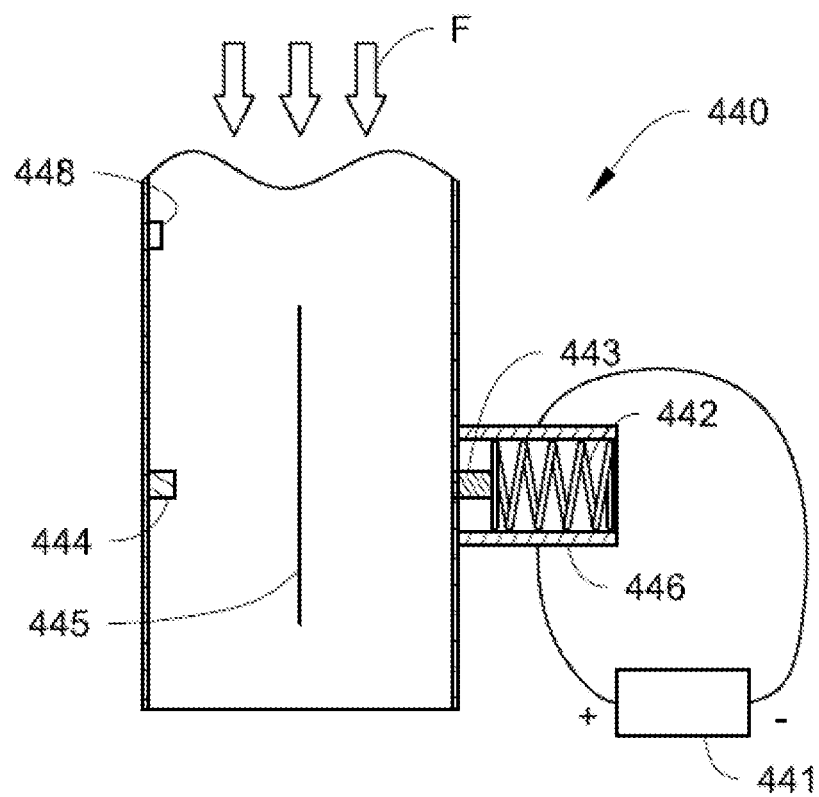
FIG. 5C schematically illustrates a valve in an open state from a side view, according to an embodiment.

Referring to FIG. 5C. FIG. 5C schematically illustrates a valve in an open state from a side view, according to an embodiment. The spring 442 can be connected with the plunger 443, and the movement of the spring 442 can cause the movement of the plunger 443. In an embodiment, when the spring 442 contracts, the plunger 443 retracts and no longer supports the leaf 445, which causes the leaf 445 to rotate to an open position due to, for example, the urine pressure within the urinary catheter 400. As such, the valve 440 is turned on, and the urine flows through the valve 440.

Figure 5D:
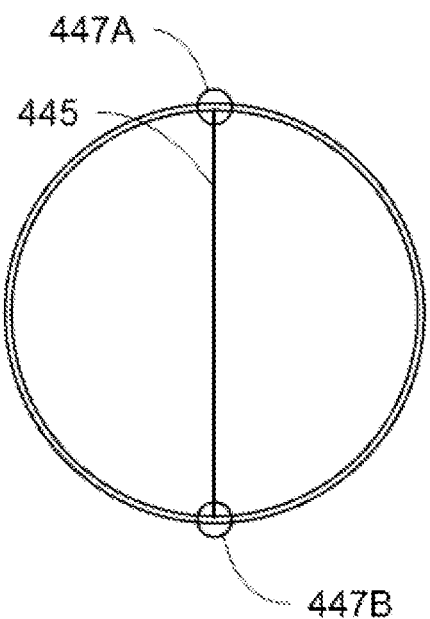
FIG. 5D schematically illustrates a valve in an open state from a top view along the urine flow F, according to an embodiment.

FIG. 5D schematically illustrates a valve in an open state from a top view along the urine flow F, according to an embodiment. The open position results as the leaf 445 rotates at or about 90 degrees relative to its closed position along the hinge 447 A and B. The leaf 445 is about parallel to the urine flow direction F at the open position.

After the user or patient voids, the leaf 445 can return back to the closed position due to the pressure drop within the urinary catheter 400. In an embodiment, when the spring 442 expands, the plunger 443 is pushed back under the leaf 445 for closing the valve 440.

Referring to FIGS. 5A and 5C, the valve 440 can be a battery-powered valve. In an embodiment, the urinary catheter 400 further includes a battery 441. When the urinary catheter 400 is powered on, the spring 442 contracts, which causes the plunger 443 to retract to a retracted position shown in FIG. 5C, which in turn causes the leaf 445 to be in the open position due to the pressure of the flow F. As such, the valve 440 is turned on, which permits urine flowing through the valve 440.

In an embodiment, the leaf 445 can automatically return to the closed position when the urine pressure within the urinary catheter 400 drops to a desired threshold after voiding. In an embodiment, the desired threshold after voiding is the pressure within the bladder after the patient voids. The leaf 445's ability to automatically return to the closed position at the desired threshold after voiding helps prevent residual urine in the bladder from leaking through the urinary catheter 400.

In an embodiment, when the urinary catheter 400 is powered off, the spring 442 expands, which causes the plunger 443 to be pushed back to its original position, as shown in FIG. 5A. The plunger 443 supports the leaf 445 so that the leaf 445 can be maintained at the closed position until the urinary catheter 400 is powered on.

In an embodiment, the urinary catheter 400 further includes a coil 446. In an embodiment, when the urinary catheter 400 is powered on, electric current flows through the coil and generates an electromagnetic field, which causes the spring 442 to contract and, in turn, enables the plunger 443 to retract to open the valve 440. In an embodiment, when the urinary catheter 400 is powered off, the electric current stops flowing through the coil 446. The coil 446 no longer generates an electromagnetic field, which causes the spring 442 to expand and, in turn, the plunger 443 to be pushed back to its original position to close the valve 440.

In an embodiment, the valve 440 further includes a pressure sensor 448 that can detect the urine pressure within the urinary catheter 400. When the pressure reaches a desired voiding threshold, the pressure sensor 448 automatically sends a signal to notify the user or patient to void. In an embodiment, the desired voiding threshold is the pressure within a normal person's bladder that causes an urge to void. In an embodiment, the sensor includes a speaker, and the signal is a sound such as, for example, a beep sound or the like so that the patient knows the bladder pressure reaches a level that the bladder needs to be emptied. In an embodiment, the sensor includes a vibrator, and the signal is a vibration.

Figure 6:
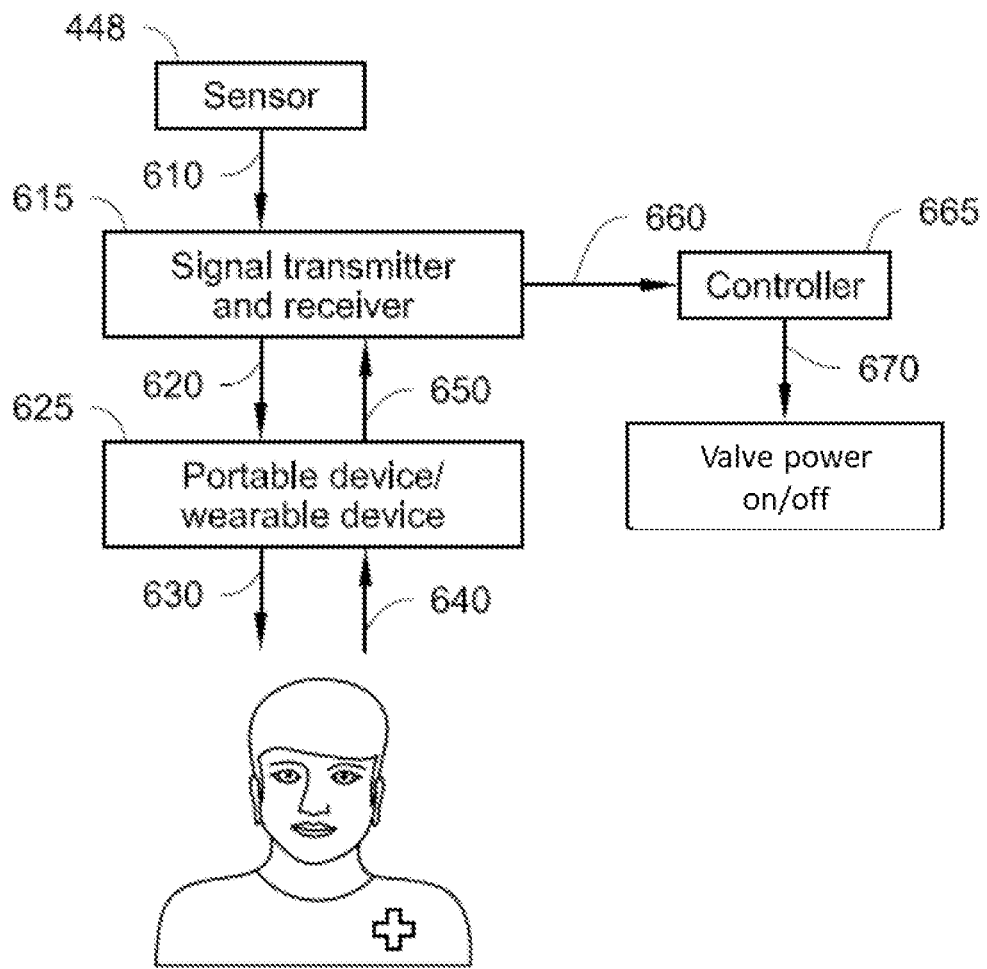
FIG. 6 schematically illustrates the use of a sensor and a portable or wearable device to control on and off of the valve, according to an embodiment.

Referring to FIG. 6, FIG. 6 schematically illustrates using a sensor and a portable or wearable device to control the closing and opening of the valve 440. In an embodiment, the valve 440 further includes a signal transmitter and receiver 615 and a controller 665. At 610, the sensor 448 detects the urine pressure within the valve 440 and transmits an electric signal encoding the detected pressure to the signal transmitter and receiver 615.

At 620, the signal transmitter and receiver 615 transmits the electric signal encoding the detected pressure to a portable/wearable device 625. In an embodiment, the signal transmitter and receiver 615 transmits the electric signal via a wire or cable. In an embodiment, the cable is a USB cable or micro-USB cable, or the like. In an embodiment, the signal transmitter and receiver 615 is a radio signal transmitter and receiver capable of communicating with the portable/wearable device 625 wirelessly via Bluetooth, NFC, RFD, network, or the like. Examples of the network include, but are not limited to, for example, Wi-Fi, cellular, 2G, 3G, 4G, 5G, 6G, or any other suitable wireless network. The portable or wearable device 625 includes but not be limited to, for example, a smartphone, smartwatch, tablet, or the like. In an embodiment, the sensor 448 communicates with the portable/wearable device 625 through an application installed in the device.

At 630, the portable/wearable device 625 receives the radio signal transmitted from the signal transmitter and receiver 615. The portable/wearable device 625 can include an application to determine if the detected pressure reaches the desired voiding threshold or the desired threshold after voiding and then generate a notice such as, for example, a sound, vibration, message, phone call, or a combination thereof to notify a user to turn on or shut off the valve 440. The user can be the patient or a caregiver of the patient.

At 640, the user turns on or shuts off the valve 440 through the application. In an embodiment, the application or sensor is configured to automatically shut off the valve 440 when the urine pressure is below the desired threshold after voiding.

At 650, the portable device/wearable device 625 sends the user's command to the signal transmitter and receiver for turning on or shutting off the valve 440.

At 660, the signal transmitter and receiver sends the user's command to the controller 625. At 670, the controller 625 turns on or off the power of the valve 440 per the user's command.

In an embodiment, the urinary catheter 440 further includes a urine storage bag or container that fluidly connects to the urine passage 105 for receiving and storing urine exiting from the valve 440. It is appreciated that the urinary catheter 100 and the urethral plug 200 can also include the urine storage bag or container for receiving and storing urine exiting from the urine passage thereof.

In an embodiment, the urethral catheter and plug discussed above not only prevent microbes from migrating into the bladder but also inhibit and/or kill microbes. In an embodiment, structures of the urinary catheter or plug, including the urinary catheter 100, the urethral plug 200, the urethral plug 300, and the urinary catheter 400 discussed above, can independently include an antimicrobial material, for example, an antimicrobial polymer material. The antimicrobial material can prevent catheter-associated urinary tract infections (CAUTI). A variety of antimicrobial materials may suitably be used. In an embodiment, a suitable antimicrobial material may include a N-halogenated amino acid or a derivative thereof. In an embodiment, a suitable antimicrobial material may include an antibiotic. In an embodiment, a suitable antimicrobial material may comprise a polymeric composite comprising a polymer and an antimicrobial particle. In an embodiment, the antimicrobial particle may include one or more of (nano)silver, copper, and, keratin, and the like. In an embodiment, a suitable antimicrobial material comprises a polymer material where an antimicrobial particle is embedded. In an embodiment, an antimicrobial particle may be coated onto the polymer material. In an embodiment, the antimicrobial material is coated on a surface of the portions or elements of the urinary catheter or plug. In an embodiment, the urinary catheter or plug can be coated with material(s) that can inhibit or prevent infection(s). In an embodiment, the material(s) can inhibit biofilm(s). In an embodiment, the material(s) include heparin. In an embodiment, the material(s) consist of heparin. Various methods can be employed to contact or coat the surfaces of the urinary catheter or plug with an antimicrobial agent. For example, one method would be to soak the surfaces of the urinary catheter or plug with an antimicrobial-containing solution.

Figure 7A:
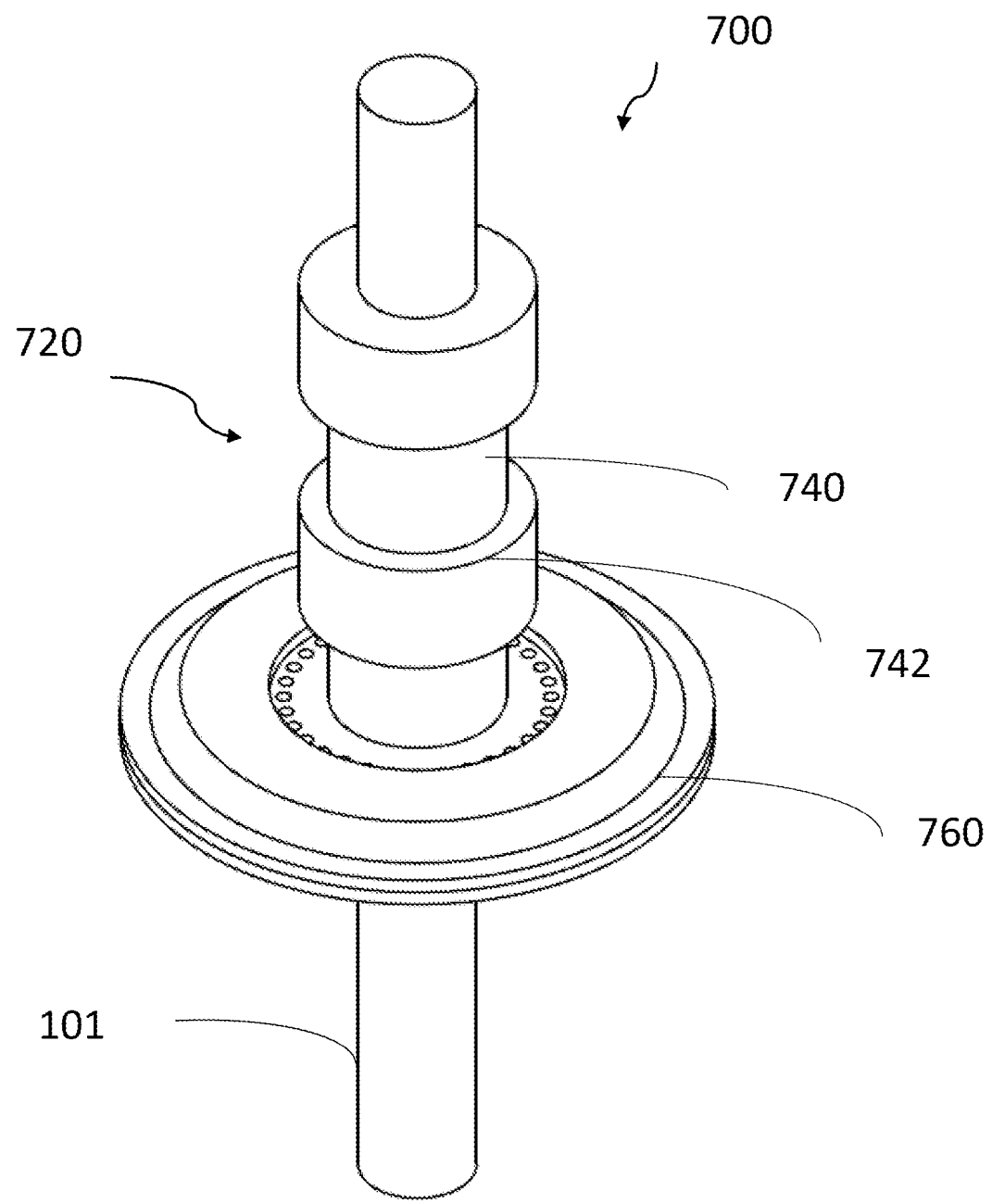
FIG. 7A schematically shows a side view of a platform, according to an embodiment.

Referring to FIG. 7A, FIG. 7A schematically shows a side view of platform 720, according to an embodiment. The platform 720 can be an embodiment of the platform 120 and 220. The platform 720 is disposed on the elongation body 101 of a urinary catheter 700 similar to the urinary catheter 100, the urethral plug 200, and the urinary catheter 400. In an embodiment, the platform 720 can slide along the elongation body 101 to adjust its position. In an embodiment, a user can apply, spray, or paint an adhesive and/or cement onto the platform 120 or the elongation body 101 and then adjust the platform 720 to a suitable position. When the adhesive and/or cement takes effect, the platform 720 is adhered to the elongation body 101. The platform 720 includes a holder 740 and a sealing structure 760. In an embodiment, the holder 740 is connected or attached to the sealing structure 760. The sealing structure 760 adheres the platform 720 onto the urethral mucous membrane and/or external orifice. A user can grab the holder 740 to detach the platform 720 from the adhered mucous membrane and/or orifice when the user wants to remove the urinary catheter 700. In an embodiment, the holder 740 includes a ridge 742 to facilitate taking off the urinary catheter 700.

Figure 7B:
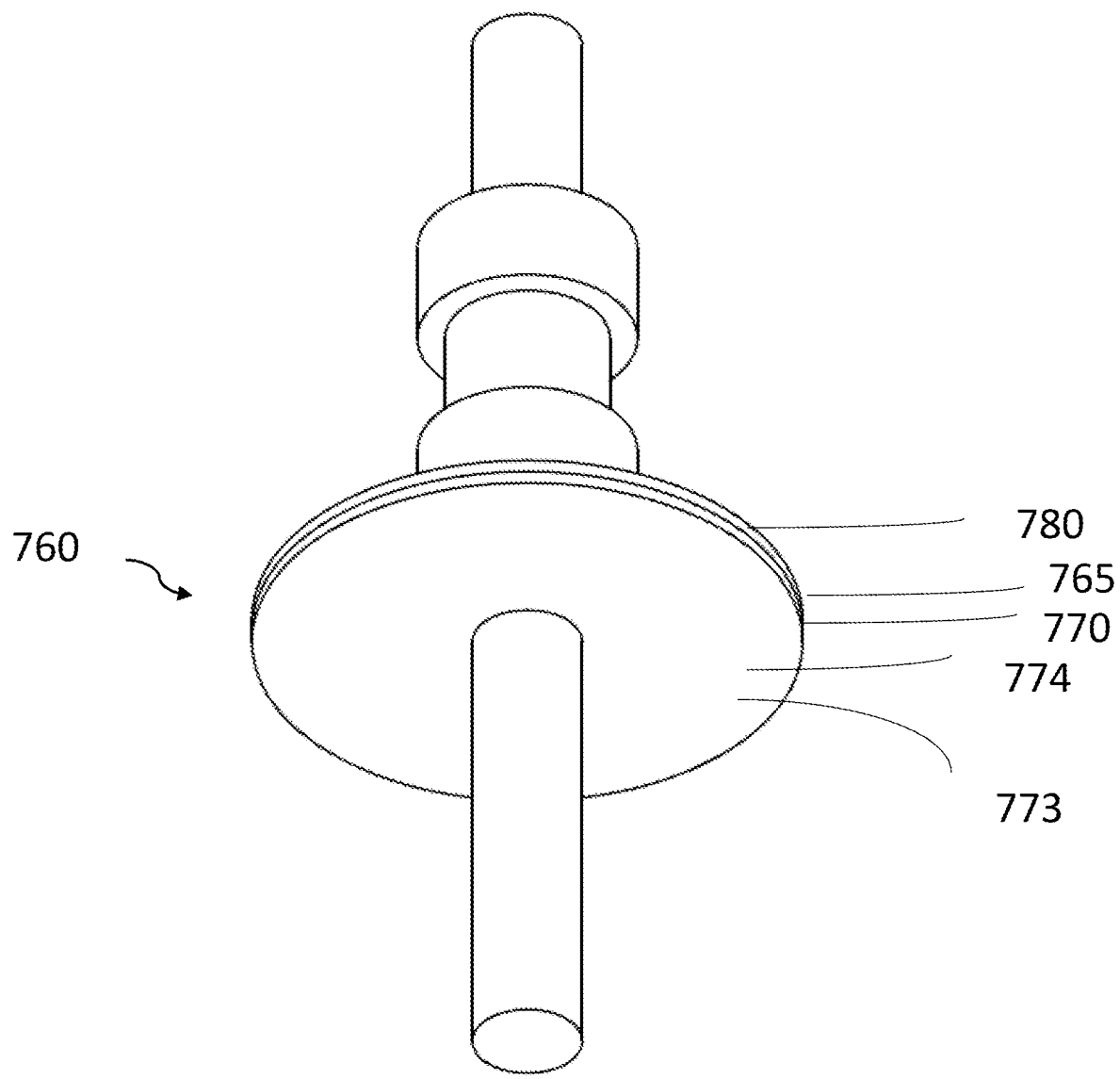
FIG. 7B schematically shows a tilt view of the platform of FIG. 7A, according to an embodiment.

Referring to FIG. 7B, FIG. 7B schematically shows a tilted view of the platform 720, according to an embodiment. The sealing structure 760 includes a first sealing structure 770, a support structure 765, and a second sealing structure 780. The first sealing structure 770 includes a first adhesive surface 773 for adhering the platform 720 onto the urethral mucous membrane and/or orifice. In an embodiment, the first adhesive surface 773 contains an adhesive or cement. In an embodiment, the first adhesive surface 773 is covered by a cover 774, such as, for example, a liner, when the platform 720 is manufactured. A user can take or peel off the cover 774 to expose the first adhesive surface 773 before or when the platform 720 is in place for use. In an embodiment, the first adhesive surface 773 is formed by applying, spraying, or painting an adhesive or cement thereon before use.

Figure 7C:
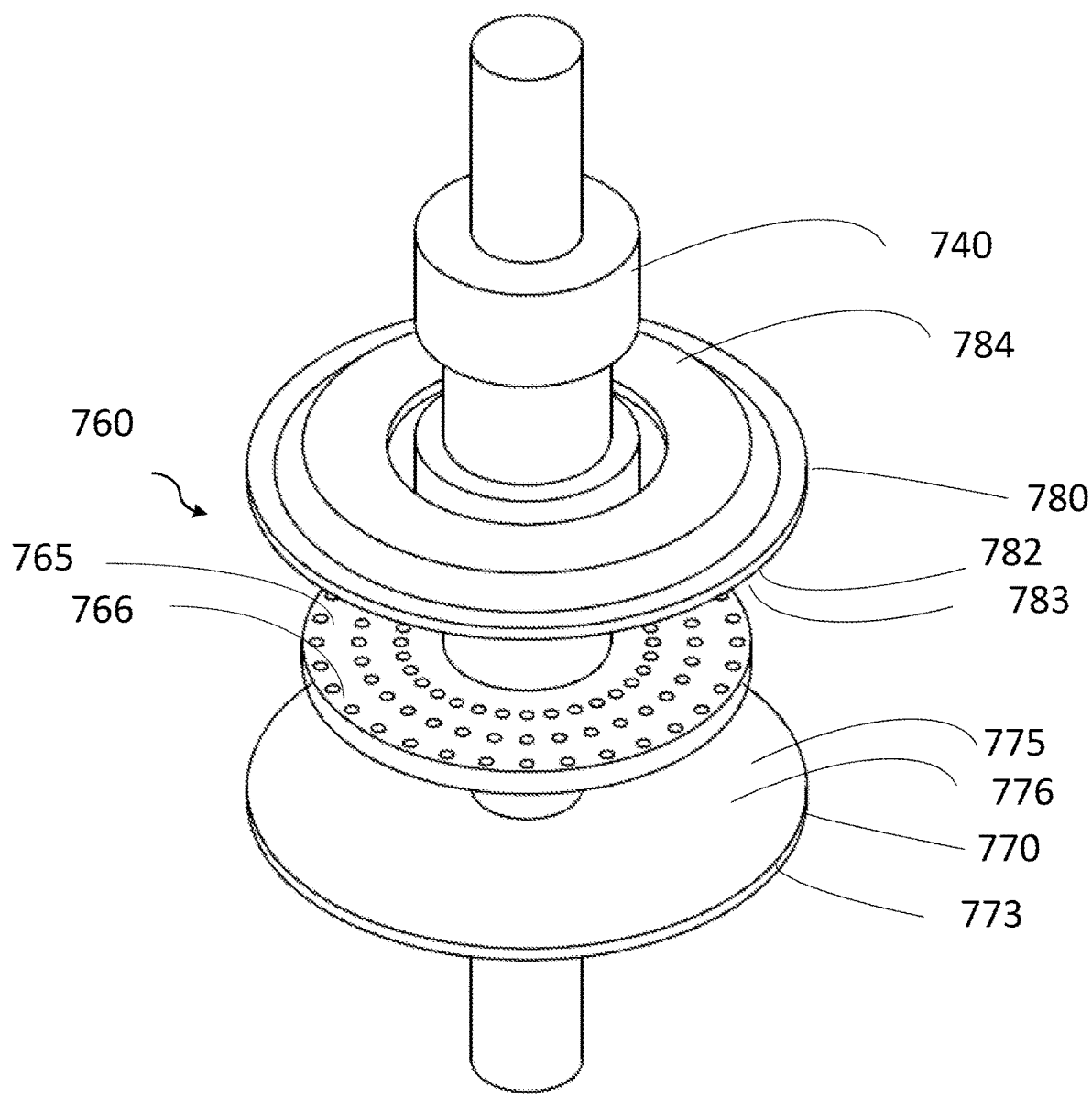
FIG. 7C schematically shows an exploded view of the platform of FIG. 7A, according to an embodiment Like reference numbers represent like parts throughout.

Referring to FIG. 7C, FIG. 7C schematically shows an exploded view of the sealing structure 760, according to an embodiment. The support structure 765 can be disposed between the first sealing structure 770 and the second sealing structure 780. In an embodiment, the support structure 765 is sandwiched between the first sealing structure 770 and the second sealing structure 780. In an embodiment, the support structure 765 is connected or attached to the holder 740. In an embodiment, the support structure 765 and the holder 740 are a unitary one-piece construction. In an embodiment, the support structure 765 is molded to the holder 740.

The first sealing structure 770 can further includes a second adhesive surface 775 that opposes the first adhesive surface 773 and faces the support structure 765. In an embodiment, the second adhesive surface 775 is covered by a cover 776, such as, for example, a liner, when the platform 720 is manufactured. A user can take or peel off the cover 774 to expose the second adhesive surface 775 before or when the platform 720 is in place for use. In an embodiment, the first sealing structure 770 is a double-sided tape. In an embodiment, the second adhesive surface 775 is formed by applying, spraying, or painting an adhesive and/or cement thereon before use.

The second sealing structure 780 includes a first side 782 and a second side 784. The first side 782 opposes the second side 784 and faces the support structure 765. The first side 782 is provided with an adhesive and/or cement. In an embodiment, the first side 782 is covered by a cover 783, such as, for example, a liner, when the platform 720 is manufactured. A user can take or peel off the cover 783 to expose the adhesive and/or cement before or when the platform 720 is in place for use. In an embodiment, the second sealing structure 780 is a single-sided tape. In an embodiment, the adhesive or cement is applied, sprayed, or painted on the first side 782 before use.

The first adhesive surface 773 of the first sealing structure 770 adheres to the urethral mucous membrane and/or orifice to seal the urethra. The second adhesive surface 775 of the first sealing structure 770 adheres to one side of the support structure 675, and the first side 782 of the second sealing structure 780 adheres to the other side of the support structure 765, forming a sandwich structure, in which the support structure 765 is sandwiched between the first sealing structure 770 and the second sealing structure 780. The sandwich structure not only seals the urethra but also attaches to the elongation body 101, allowing a user to detach the first sealing structure 770 from the adhered tissues by pulling the urinary catheter 700 or the holder 740.

The first sealing structure 770 can adhere to the support structure 765 more strongly than to the urethral mucous membrane and/or orifice so that a user to detach the first sealing structure 770 from the urethral mucous membrane and/or orifice by pulling the catheter 700 or the holder 740. In an embodiment, the support structure 765 has a plurality of pores 766 allowing adhesive and/or cement provided on the first side 782 and the second adhesive surface 775 to pass through, which can enhance the adherence of the first sealing structure 770 to the support structure 765. In an embodiment, the first sealing structure 770 and the second sealing structure 780 are larger than the support structure 765 in area so that portions of the first sealing structure 770 and the second sealing structure 780 can stick together directly to enhance the adherence of the first sealing structure 770 onto the support structure 765. In an embodiment, the first sealing structure 770 and the second sealing structure 780 have a diameter larger than the support structure 765.

In an embodiment, the first side 782 can include an acrylic adhesive or any other suitable adhesive/cement. In an embodiment, the first adhesive surface 773 and/or the second adhesive surface 775 can include a hydrocolloid adhesive or any other suitable adhesive/cement.

The material, softness, and pliability of the sealing structure 760 are similar to those discussed above for the platform 120. In an embodiment, the material, softness, and pliability of the holder 740 are similar to those discussed above for the attachment 203 and/or the distal portion 180

The first sealing structure 770, the support structure 765, and the second sealing structure can be any suitable form or have any suitable shape, including but not limited to round, oval, rectangle, etc. In an embodiment, the first sealing structure 770, the support structure 765, and the second sealing structure have a disk shape. In an embodiment, the first sealing structure 770, the support structure 765, and the second sealing structure are deformable and can adopt a shape to mate the surface contour of the urethral membrane and/or orifice.

It is appreciated that the devices in this disclosure, including the urinary catheter 100, the urethral plug 200, the urethral plug 300, the urinary catheter 400, and the urinary catheter 700 can apply to both male and female patients with or without apparent modification. Such modification should be understood as being within the scope of this disclosure. It is also appreciated that the devices in this disclosure can be used in preventing, reducing, and managing urinary tract infections.

ASPECTS

Any one of aspects 1-23 is combinable to any one of aspects 24-28.

Aspect 1. A device for managing urinary incontinence of a patient in need thereof, comprising one or more materials selected from the group consisting of a silicone material, a thermoplastic material, a thermos-impression material, an adhesive, and a cement for sealing the urethra, wherein the materials are non-tissue irritating, non-allergenic materials, the adhesive or cement is capable of adhering the device to a urethra mucous membrane or orifice and sealing the gaps therebetween.

Aspect 2. The device of aspect 1, wherein that the silicone material and the thermoplastic material are capable of softening at a body temperature of the urethra to fit a contour of an inner surface of the urethra and/or a terminal end of the urethra and obtain a seal or adherence sufficient to prevent bacterial migration into the urethra and/or bladder.

Aspect 3. The device of any one of aspects 1 and 2, wherein the thermoplastic material is a thermoplastic elastomer includes at least one selected from the group consisting of styrenic block copolymers, thermoplastic olefin blends (TPO), thermoplastic polyurethanes (TPU), elastomeric alloys (TPV), thermoplastic copolyester (COPE), and polyether block amides (PEBAX),
the adhesive or cement is selected from the group consisting of a silicone adhesive, a hydrocolloid adhesive, an acrylic adhesive, and a combination thereof,
and the thermo-impression material is selected from the group consisting of a polysiloxane material, a polyether material, and a combination thereof.

Aspect 4. The device of any one of aspects 1-3, wherein the thermoplastic elastomer has hardness in a range of 10 to 40 on the Shore 00 scale of hardness at body temperature.

Aspect 5. The device of any one of aspects 1-4, wherein the thermoplastic elastomer has a hardness in a range of 40 to 65 on the Shore 00 scale of hardness at body temperature.

Aspect 6. The device of any one of aspects 1-5, wherein the device further comprises an inner body, and the thermoplastic elastomer is provided around the inner body.

Aspect 7. The device of aspect 6, wherein the inner body is an elastomer.

Aspect 8. The device of any one of aspects 1-5, wherein the device further comprises an elongated body insertable into a urethra through an external opening of a urethra,
the thermoplastic elastomer constitutes a platform around the elongated body,
the adhesive is disposed on a first surface of the platform, and
the first surface contacts the mucous membranes of the urethra or urethra orifice.

Aspect 9. The device of aspect 8, wherein the platform is movable axially along the elongated body, and the platform can be retained at different positions of the elongated body.

Aspect 10. The device of aspect 9, wherein the device further comprises a retainer for retaining the platform at different positions of the elongated body, and the platform is axially movable along the retainer.

Aspect 11. The device of aspect 9, wherein the platform contains a second adhesive disposed at a second surface of the platform, where the second adhesive directly adheres the platform to the elongated body,
the second adhesive is releasable and reusable so that the platform is capable of dislodging from the elongated body by force and re-adhering to a new position at the elongated body, and
the second adhesive is selected from the group consisting of silicone adhesive, hydrocolloid adhesive, and acrylic adhesive.

Aspect 12. The device of aspect 11, wherein the second adhesive is a silicone adhesive or cement.

Aspect 13. The device of any one of aspects 8-12, wherein the elongated body includes a proximal portion and a distal portion opposing the proximal portion,
the device further comprises an inflatable balloon disposed at the proximal portion, and the inflatable balloon includes a thermoplastic elastomer and/or an adhesive capable of sealing an internal orifice of the urethra.

Aspect 14. The device of any one of aspects 8-13, wherein the elongated body includes a urine passage.

Aspect 15. The device of any one of aspects 13-14, wherein the proximal portion is firmer than the distal portion.

Aspect 16. The device of any one of aspects 13-15, wherein the proximal portion has a hardness in a range of 40 to 100 on the Shore A scale of hardness at body temperature, and the distal portion has a hardness in a range of 0 to 40 on Shore A scale of hardness.

Aspect 17. The device of any one of aspects 13-16, wherein the device further includes an inflation tube and an inlet, and the inflation tube is in fluid communication with the balloon.

Aspect 18. The device of any one of aspects 1-17, wherein the device further includes a urination controller for controlling urination.

Aspect 19. The device of aspect 18, wherein the urination controller includes a plug or valve.

Aspect 20. The device of aspect 19, wherein the valve is a palpitatable discharge valve.

Aspect 21. The device of aspect 19, wherein the valve comprises a battery, a coil, a spring, a plunger, and a leaf,
wherein the spring is connected with the plunger,
the coil generates an electromagnetic field when electric current flows through the coil, which causes the spring to contract and, in turn, causes the plunger to retract to turn on the valve, and
when the electric current stops flowing through the coil, the coil no longer generates an electromagnetic field, and the spring expands, which in turn causes the plunger to extend to close the valve.

Aspect 22, the device of aspect 21, wherein the valve further comprises a sensor for detecting a urine pressure in the urethra, and
when the urine pressure reaches a desired thresholds pressure, the sensor sends a signal to notify a patient to turn on the valve to void.

Aspect 23, the device of aspect 1-22, comprising a urine collection bag or container that fluidly connects with the urine passage for receiving and storing urine exited from the urine passage.

Aspect 24. A method for managing urinary incontinence, comprising inserting the device of any one of aspects 1-23 through the external orifice of urethra, wherein the platform is disposed within the urethra and seals the urethra.

Aspect 25. The method of aspect 24, wherein inserting the device includes inserting the balloon inside a bladder.

Aspect 26. The method of aspect 25, further comprising inflating the balloon.

Aspect 27. The method of aspect 26, further comprising pulling the balloon so that the balloon is in sealing contact with a neck of the bladder.

Aspect 28. The method of aspect 27, wherein the platform seals the urethra, and the balloon seals the internal orifice of the urethra.

I claim:

1. A device for managing urinary incontinence of a patient in need thereof, comprising:
   an elongated body insertable into a urethra through an external opening of the urethra,
   a platform disposed around the elongated body,
   a urine passage disposed within the elongated body,
   an inflatable balloon, and
   a valve, wherein
   the platform comprises a first sealing structure, a support structure, and a second sealing structure,
   the support structure is fixable to the elongated body, and
   the first sealing structure includes a first adhesive surface and a second adhesive surface opposing the first adhesive surface, wherein
      the first adhesive surface contains a first adhesive or cement that is capable of adhering the platform to a urethral mucous membrane or orifice, and
      the second adhesive faces the support structure and contains a second adhesive or cement that is capable of adhering the first sealing structure to the support structure.

2. The device of claim 1, wherein the platform further comprises a silicone, a thermo-impression material, or thermoplastic material capable of softening at a body temperature of the urethra so that the silicone, thermo-impression material, or thermoplastic material is adapted to a shape fitting a contour of an inner surface of the urethra and/or a terminal end of the urethra.

3. The device of claim 2, wherein the thermoplastic material is a thermoplastic elastomer that includes at least one selected from the group consisting of styrenic block copolymers, thermoplastic olefin blends (TPO), thermoplastic polyurethanes (TPU), elastomeric alloys (TPV), thermoplastic copolyester (COPE), and polyether block amides (PEBAX), and
   the thermo-impression material is a polysiloxane material or a polyether material or a combination thereof.

4. The device of claim 2, wherein the silicone is a silicone rubber or a liquid silicone rubber.

5. The device of claim 1, wherein the support structure comprises an adhesive surface containing a adhesive or cement that is capable of adhering the platform directly to the elongated body, and
   the adhesive or cement is releasable and reusable so that the platform is movable axially along the elongated body and retained at different positions of the elongated body.

6. The device of claim 1, wherein the first adhesive surface is covered with a release cover.

7. The device of claim 1, wherein each of the first and the second adhesive or cement are independently selected from the group consisting of a silicone adhesive or cement, a hydrocolloid adhesive or cement, an acrylic adhesive or cement, and a combination thereof.

8. The device of claim 1, wherein the inflatable balloon includes a thermoplastic elastomer capable of softening at a body temperature for sealing an internal urethral orifice.

9. The device of claim 1, wherein the inflatable balloon includes an adhesive capable of sealing an internal orifice of the urethra, and the adhesive is one or more selected from the group consisting of silicone adhesive, a hydrocolloid adhesive, and an acrylic adhesive.

10. The device of claim 1, further comprising a sensor to detect a urine pressure within the valve, the sensor is configured to send a signal to notify a user to turn on or shut off the valve when the urine pressure reaches a desired thresholds pressure.

11. The device of claim 10, wherein the sensor further includes a speaker or vibrator, and the signal is respectively a sound or a vibration.

12. The device of claim 10, wherein the valve further comprises a signal transmitter and receiver and a controller,
   the signal transmitter and receiver receives an electric signal encoding the detected urine pressure and transmits the electric signal wirelessly to a portable or wearable device.

13. The device of claim 12, wherein the portable or wearable device is a smartphone, a smartwatch, or a tablet.

14. The device of claim 1, wherein the valve comprising:
   a battery;
   a coil;
   a spring;
   a plunger; and
   a leaf,
   wherein the spring is connected with the plunger, and the plunger is connected with the leaf,
   the coil generates an electromagnetic field when electric current flows through the coil, which causes the spring to contract and in turn causes the plunger to retract to turn on the valve, and
   when the electric current stops flowing through the coil, the coil no longer generates the electromagnetic field, and the spring expands, which in turn causes the plunger to extend to close the valve.

15. The device of claim 1, wherein the second sealing structure includes a first side and a second side opposing the first side, the first side faces the support structure and contains a third adhesive or cement that is capable of adhering the second sealing structure to the support structure.

16. The device of claim 15, wherein the first adhesive surface, second adhesive surface, and the first side are covered with a release cover.

17. The device of claim 15, wherein the first sealing structure adheres to the support structure more strongly than to the urethral mucous membrane or orifice.

18. The device of claim 1, wherein the first sealing structure and the second sealing structure have a size larger than the support structure so that a portion of the first and second sealing structure adhere to each other.

19. The device of claim 1, wherein the support structure comprises a plurality of pores.

20. A method for managing urinary incontinence of a patient, comprising:
   inserting the device of claim 1 through the external orifice of the urethra of a patient in need thereof,
   inflating the inflatable balloon that includes a thermoplastic elastomer and/or a silicone adhesive, pulling the inflatable balloon so that the thermoplastic elastomer and/or adhesive is in sealing contact with a neck of the bladder, and adjusting the platform to a suitable position at the elongated body for sealing the urethra, wherein the platform seals the urethra, and the balloon seals the internal orifice of the urethra.

21. The method of claim 10, wherein the first adhesive surface is covered by a release cover, and the method further comprises taking off the release cover to expose the first adhesive surface.

22. The method of claim 20, further comprising detecting a urine pressure within the device.

23. The method of claim 22, further comprising transmitting a signal encoding the detected urine pressure to a portable or wearable device.

24. The method claim 20, further comprising notifying a user with an alert to turn on and/or shut off the valve.

25. The method of claim 24, wherein the alert is a sound or vibration.

* * * * *